(12) United States Patent
Dickie et al.

(10) Patent No.: US 11,043,144 B2
(45) Date of Patent: Jun. 22, 2021

(54) SYSTEMS AND METHODS FOR PROVIDING AN INTERACTIVE DEMONSTRATION OF AN ULTRASOUND USER INTERFACE

(71) Applicant: Clarius Mobile Health Corp., Burnaby (CA)

(72) Inventors: Kris Dickie, Vancouver (CA); Trevor Stephen Hansen, North Vancouver (CA); Siavash Khallaghi, Vancouver (CA)

(73) Assignee: Clarius Mobile Health Corp., Vancouver (CA)

( * ) Notice: Subject to any disclaimer, the term of this patent is extended or adjusted under 35 U.S.C. 154(b) by 183 days.

(21) Appl. No.: 16/038,050

(22) Filed: Jul. 17, 2018

(65) Prior Publication Data

US 2019/0043387 A1 Feb. 7, 2019

Related U.S. Application Data

(60) Provisional application No. 62/541,624, filed on Aug. 4, 2017.

(51) Int. Cl.
*G09B 23/28* (2006.01)
*A61B 8/00* (2006.01)

(52) U.S. Cl.
CPC ............ *G09B 23/285* (2013.01); *A61B 8/465* (2013.01); *A61B 8/467* (2013.01); *A61B 8/468* (2013.01); *A61B 8/565* (2013.01); *G09B 23/286* (2013.01)

(58) Field of Classification Search
CPC .... G09B 23/285; G09B 23/286; A61B 8/465; A61B 8/467; A61B 8/565; A61B 8/468
See application file for complete search history.

(56) References Cited

U.S. PATENT DOCUMENTS

| | | | |
|---|---|---|---|
| 6,468,212 B1 | 10/2002 | Scott et al. | |
| 6,669,633 B2 | 12/2003 | Brodsky et al. | |
| 7,835,892 B2 | 11/2010 | Butsev et al. | |
| 2007/0264984 A1* | 11/2007 | Stavenow | H04M 1/72403 455/414.1 |
| 2007/0288251 A1* | 12/2007 | Ebrom | D06F 33/00 705/1.1 |
| 2010/0055657 A1* | 3/2010 | Goble | G09B 23/286 434/262 |
| 2011/0306025 A1 | 12/2011 | Sheehan et al. | |
| 2013/0065211 A1 | 3/2013 | Amso et al. | |

(Continued)

*Primary Examiner* — Malina D. Blaise
(74) *Attorney, Agent, or Firm* — Julian Ho

(57) ABSTRACT

Systems and methods for providing an interactive demonstration of an ultrasound user interface are generally described herein. The method may include, at a multi-use display device: receiving a demonstration ultrasound dataset from a server; displaying, on the ultrasound user interface, ultrasound data from the demonstration ultrasound dataset; receiving input, on the ultrasound user interface, to interact with the ultrasound data from the ultrasound dataset; and in response to the received input, updating the ultrasound user interface so that the ultrasound user interface corresponds to the received input, the updated ultrasound user interface appearing substantially similar to an appearance of the ultrasound user interface that is displayed if the received input is received during display of a live ultrasound image feed.

20 Claims, 10 Drawing Sheets

(56) References Cited

U.S. PATENT DOCUMENTS

| | | | |
|---|---|---|---|
| 2015/0271436 A1* | 9/2015 | Qin | G11B 27/00 |
| | | | 386/230 |
| 2015/0363207 A1* | 12/2015 | Mahajan | H01M 10/44 |
| | | | 713/100 |
| 2017/0105701 A1* | 4/2017 | Pelissier | G16H 30/40 |
| 2018/0261257 A1* | 9/2018 | Suzuki | G06Q 30/02 |
| 2018/0336803 A1* | 11/2018 | Patil | A61B 8/523 |

* cited by examiner

SYSTEMS AND METHODS FOR PROVIDING AN INTERACTIVE DEMONSTRATION OF AN ULTRASOUND USER INTERFACE

CROSS-REFERENCE TO RELATED APPLICATIONS

This application claims the benefit of U.S. Provisional Patent Application No. 62/541,624 entitled "SYSTEMS AND METHODS FOR DEMONSTRATING OPERATION OF AN ULTRASOUND IMAGING SYSTEM" filed on Aug. 4, 2017, which is incorporated by reference it its entirety in this disclosure.

FIELD

The present disclosure relates generally to ultrasound imaging, and in particular, to systems and methods for providing an interactive demonstration of the user interface of an ultrasound imaging system.

BACKGROUND

Ultrasound imaging systems provide an easy and accessible method of performing medical diagnostic imaging. Traditional ultrasound imaging systems typically include several components all provided by the same manufacturer: an ultrasound probe (also called a transducer) that transmits and receives ultrasound energy; processing electronics and software that process the ultrasound signals from the ultrasound probe to generate ultrasound images; a proprietary display for displaying the generated ultrasound images; and user controls that allow for manipulation of imaging and viewing parameters. Since a single manufacturer typically provides all these various components, demonstration of these traditional ultrasound systems (e.g., for a potential purchaser considering purchase of an ultrasound system) usually involve in-person use of the entire ultrasound system. For example, an ultrasound system manufacturer may ship the entire system to a potential purchaser to allow them to perform live scanning and manipulate the user controls. Alternatively, the ultrasound system manufacturer may invite a potential purchaser to a designated location where a demonstration system can be made available for the potential purchaser to try.

Some modern ultrasound machines have been designed to be smaller and more portable. Instead of including a proprietary display, some such machines provide only an ultrasound probe that encompasses suitable connectivity electronics/software. This ultrasound probe can then connect to a multi-use electronic display device (e.g., a smartphone or tablet computer) for display of generated ultrasound images. The display device may also receive user input to modify imaging and viewing parameters.

When deciding whether to purchase these smaller ultrasound machines, potential purchasers may still desire to try the machine. Although these machines are smaller and easier to transport, sending of the machine to a potential purchaser may require time and cause delay before the potential purchaser can try various aspects of the ultrasound imaging experience.

There is thus a need for improved methods of demonstrating the operation of the user interface for an ultrasound system. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
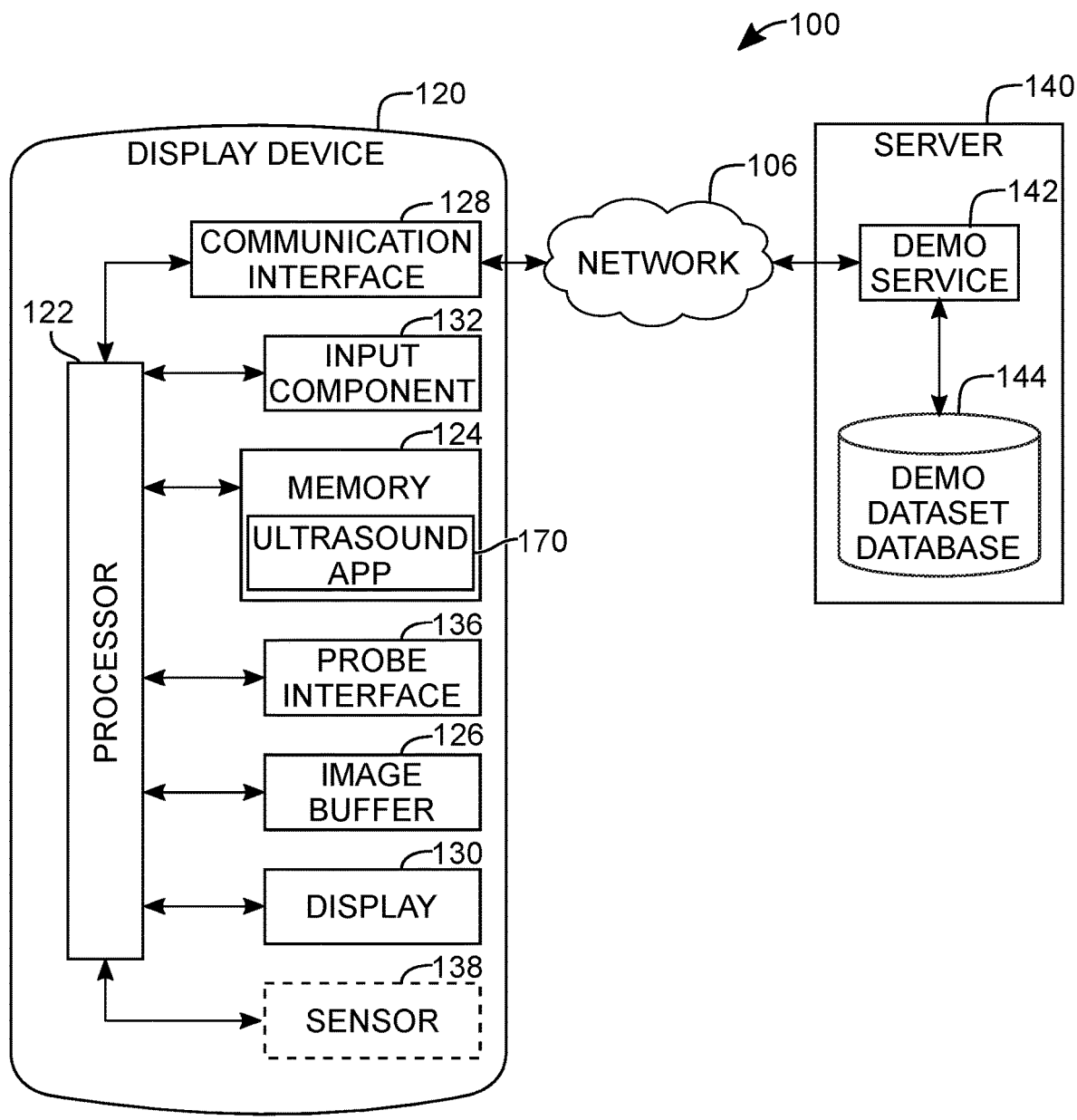
FIG. 1 shows a functional block diagram of a system for providing an interactive demonstration of an ultrasound user interface, in accordance with at least one embodiment of the present invention.

In a first broad aspect of the present disclosure, there is provided a method of providing an interactive demonstration of an ultrasound user interface, the method including, at a multi-use display device: receiving a demonstration ultrasound dataset from a server; displaying, on the ultrasound user interface, ultrasound data from the demonstration ultrasound dataset; receiving input, on the ultrasound user interface, to interact with the ultrasound data from the ultrasound dataset; and in response to the received input, updating the ultrasound user interface so that the ultrasound user interface corresponds to the received input, the updated ultrasound user interface appearing substantially similar to an appearance of the ultrasound user interface that is displayed if the received input is received during display of a live ultrasound image feed.

In some embodiments, when displaying the ultrasound user interface, user interface controls for modifying image acquisition parameters are non-controllable.

In some embodiments, the demonstration ultrasound dataset is acquired at a single imaging depth. In some embodiments, the received input includes changing the imaging depth of the displayed ultrasound data from a first imaging depth to a second imaging depth, and updating the ultrasound user interface includes performing a digital zoom operation.

In some embodiments, the method further includes: receiving another demonstration ultrasound dataset from the server; and when updating the ultrasound user interface so that the ultrasound user interface corresponds to the received input, displaying additional ultrasound data from the another demonstration ultrasound dataset.

In some embodiments, the demonstration ultrasound dataset is acquired at a first imaging depth, and the another demonstration ultrasound dataset is acquired at a second imaging depth different from the first imaging depth, and the received input includes changing the imaging depth from that of the demonstration ultrasound dataset to that of the another demonstration ultrasound dataset.

In some embodiments, prior to the receiving the another demonstration ultrasound dataset from the server, the method further includes: determining if the received input requires downloading the another demonstration ultrasound dataset; and if determined that the received input requires downloading the another demonstration ultrasound dataset, requesting the another demonstration ultrasound dataset from the server.

In some embodiments, the demonstration ultrasound dataset and the another demonstration ultrasound dataset are received together in a demonstration ultrasound dataset collection, prior to the receiving of the input on the ultrasound user interface.

In some embodiments, the receiving of the another demonstration ultrasound dataset is performed as the ultrasound data from the demonstration ultrasound dataset is displayed.

In some embodiments, the demonstration ultrasound dataset is associated with a demonstration workflow. In some embodiments, prior to receiving the demonstration ultrasound dataset, the method further includes: receiving a list of demonstration workflows from the server; displaying the list of demonstration workflows; and receiving input selecting the demonstration workflow. In some embodiments, the demonstration workflow is associated with a virtual demonstration imaging device, and prior to receiving the demonstration ultrasound dataset, the method further includes: receiving a list of virtual demonstration imaging devices from the server; displaying the list of virtual demonstration imaging devices; and receiving input selecting the virtual demonstration imaging device associated with the virtual demonstration workflow.

In another broad aspect of the present disclosure, there is provided a multi-use display device including one or more processors and memory storing instructions for providing demonstration of an ultrasound user interface, wherein when the instructions are executed by the one or more processors, the one or more processors are configured to: receive a demonstration ultrasound dataset from a server; display the ultrasound user interface on the multi-use display device, the ultrasound user interface including ultrasound data from the demonstration ultrasound dataset; receive input, on the ultrasound user interface, to interact with the ultrasound data from the ultrasound dataset; and in response to the received input, update the ultrasound user interface so that the ultrasound user interface corresponds to the received input, the updated ultrasound user interface appearing substantially similar to an appearance of the ultrasound user interface that is displayed if the received input is received during display of a live ultrasound image feed.

In some embodiments, the one or more processors are further configured to: receive another demonstration ultrasound dataset from the server; and when updating the ultrasound user interface so that the ultrasound user interface corresponds to the received input, display additional ultrasound data from the another demonstration ultrasound dataset.

In some embodiments, the demonstration ultrasound dataset is acquired at a first imaging depth, and the another demonstration ultrasound dataset is acquired at a second imaging depth different from the first imaging depth, and the received input includes changing the imaging depth from that of the demonstration ultrasound dataset to that of the another demonstration ultrasound dataset.

In some embodiments, prior to the receiving the another demonstration ultrasound dataset from the server, the one or more processors are further configured to: determine if the received input requires downloading the another demonstration ultrasound dataset; and if determined that the received input requires downloading the another demonstration ultrasound dataset, request the another demonstration ultrasound dataset from the server.

In some embodiments, the demonstration ultrasound dataset and the another demonstration ultrasound dataset are received together in a demonstration ultrasound dataset collection, prior to the receiving of the input on the ultrasound user interface.

In some embodiments, the receiving of the another demonstration ultrasound dataset is performed as the ultrasound data from the demonstration ultrasound dataset is displayed.

In some embodiments, the demonstration ultrasound dataset is associated with a demonstration workflow.

In another broad aspect of the present disclosure, there is provided a computer readable medium storing instructions for providing demonstration of an ultrasound user interface, wherein when the instructions are executed by one or more processors of a multi-use display device, the one or more processors are configured to: receive a demonstration ultrasound dataset from a server; display the ultrasound user interface on the multi-use display device, the ultrasound user interface including ultrasound data from the demonstration ultrasound dataset; receive input, on the ultrasound user interface, to interact with the ultrasound data from the ultrasound dataset; and in response to the received input, update the ultrasound user interface so that the ultrasound user interface corresponds to the received input, the updated ultrasound user interface appearing substantially similar to an appearance of the ultrasound user interface that is displayed if the received input is received during display of a live ultrasound image feed.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

During typical operation of an ultrasound system, an ultrasound transducer emits ultrasound energy into a body of interest and receives ultrasound echoes. These echo signals are subject to series of processing steps and ultimately displayed. Operating an ultrasound system includes a combination of skills, including physically manipulating the ultrasound transducer and interacting with a user interface that displays the ultrasound image data.

The user interface enables the user to control the ultrasound imaging system. The user interface may provide a workflow for performing a particular imaging task. The user interface may provide a number of workflows that correspond to imaging a particular region of the body, commonly referred to as presets. A particular workflow may include image acquisition settings, as well as prompting for or requiring standardized measurements or annotations.

The user interface may also provide a number of controls for interacting with the ultrasound data transmitted from the ultrasound imaging transducer. For example, common functions include starting and stopping image acquisition, and adjusting gain, frequency, and imaging depth. The embodiments described herein generally provide a method of experiencing elements of the user interface of the ultrasound imaging system without being physically in possession of the ultrasound transducer or probe.

Referring to FIG. 1, shown there generally as 100 is a functional block diagram of a system for providing an interactive demonstration of an ultrasound user interface, in accordance with at least one embodiment of the present invention. System 100 may include a multi-use electronic display device 120 communicatively coupled to a server 140.

In various embodiments, multi-use electronic display device 120 may be a smartphone, tablet computer, or laptop computer. Alternatively, display device 120 may also be a custom-built tablet computer. As illustrated, the display device 120 may include a communication interface 128, input component 132, processor 122, memory 124, image buffer 126, display 130, and probe interface 136. In various embodiments, display device 120 may include a greater or fewer number of elements. For example, display device 120 may also include optional sensor 138 (shown in dotted outline and discussed below). For ease of reference, the multi-use electronic display device 120 may also be referred to simply as the "display device" herein.

Memory 124 may be any suitable memory component that stores software instructions for execution by the processor 122. For example, the software for operating and interacting with the ultrasound imaging machine may be provided in the form of a downloadable ultrasound application, or "app" 170. In various embodiments, the operating software may be distributed over an Internet connection, and made available through a suitable software distribution platform of the operating system executing on the display device 120 (e.g., the Apple™ App Store for devices executing the iOS™ operating system, or the Google™ Play Store™ for devices executing the Android™ operating system).

When such applications are executing on the display device 120, input can be received via the input component 132 to manipulate a user interface being provided by the application 170. Input component 132 may be any suitable user input component. For example, input component 132 may be a touchscreen. However, in various embodiments, input component 132 may additionally or alternatively include a keyboard, mouse, or other conventional or future developed type of user input (e.g., touch, voice, and/or three-dimensional (3D) gesture input).

In some embodiments, the user interface being provided by application 170 may also be manipulated and/or updated in response to input received by sensor 138. For example, sensor 138 may be provided as an accelerometer, gyroscope, and/or inertial measurement sensor. The user input may be manipulated in response to changes in position or orientation of display device 120 as read by the sensor 138.

The present embodiments allow for demonstration of the operation of an ultrasound machine without the ultrasound machine being physically present. Since some modern ultrasound machines may only encompass the probe portion of an ultrasound system (the probe being configured to communicate with a multi-use electronic display device 120 for display of ultrasound images), it is possible to demonstrate some elements of the user experience of such a machine without the machine being actually communicably connected to the multi-use electronic display device 120. For example, in the present embodiments, an application 170 executing on the display device 120 typically configured to receive live ultrasound image data from the ultrasound machine may be configured to operate in a demo mode. The abbreviated term "demo" and the full word "demonstration" may generally be considered interchangeable herein.

As discussed below, in this demo mode, the application 170 may not have a live connection to an ultrasound imaging device. However, it can retrieve demonstration ultrasound image data from a server 140 and provide a user interface that allows manipulation of the demonstration ultrasound image data as if it was receiving live ultrasound image data from an ultrasound machine. With modern small and portable ultrasound machines that allow for distribution of the ultrasound machine separate from the software that executes on a display device 120 for communicating with the machine, it is possible for a user with a compatible display device 120 to obtain the software application 170 (e.g., via the online app stores of an operating system executing on the display device 120), without being in possession of the accompanying ultrasound imaging machine. This may allow a user to experience certain elements of the user interface provided by the ultrasound application 170 for an ultrasound machine, without requiring the user to be in actual physical possession of the ultrasound machine.

The probe interface 136 may allow the display device 120 to connect to, and communicate with, the ultrasound machine. Depending on the nature of the ultrasound machine, different component(s) of the display device 120 may be considered the probe interface 136. For example, in some embodiments, the ultrasound machine may be provided as a wired ultrasound probe that connects via a data port (e.g., Universal Serial Bus (USB), Lightning™ or other suitable data port) available on the display device 120. Additionally or alternatively, the ultrasound machine may be provided in the form of an ultrasound probe that connects wirelessly via suitable wireless communication protocol(s)

(e.g., Bluetooth™, Wi-Fi™, and any other similar or future-developed wireless communication protocol). In the wireless scenario, the wireless network or protocol interface may be considered the probe interface 136.

The present embodiments may be practiced with any suitable ultrasound probe or transducer that can connect to a multi-use display device 120. As used herein, the terms ultrasound imaging "machine", "probe", "device", "scanner", "transducer", or "unit" may be interchangeable, and such terms generally refer to any type of ultrasound imaging device that can connect to display device 120 to provide ultrasound data.

The communication interface 128 may allow the display device 120 to communicate with the server 140 via network 106 (e.g., the Internet). In various embodiments, the communication interface 128 may be any suitable network interface that allows the ultrasound software 170 executing on the display device 120 to make a network connection to server 140.

Server 140 may include a demo service 142 and ultrasound demo dataset database 144. Upon request from display device 120, demo service 142 may be configured to retrieve one or more demonstration ultrasound datasets from ultrasound demo dataset database 144 for transmission to the ultrasound app 170 executing on the display device 120.

Figure 2:
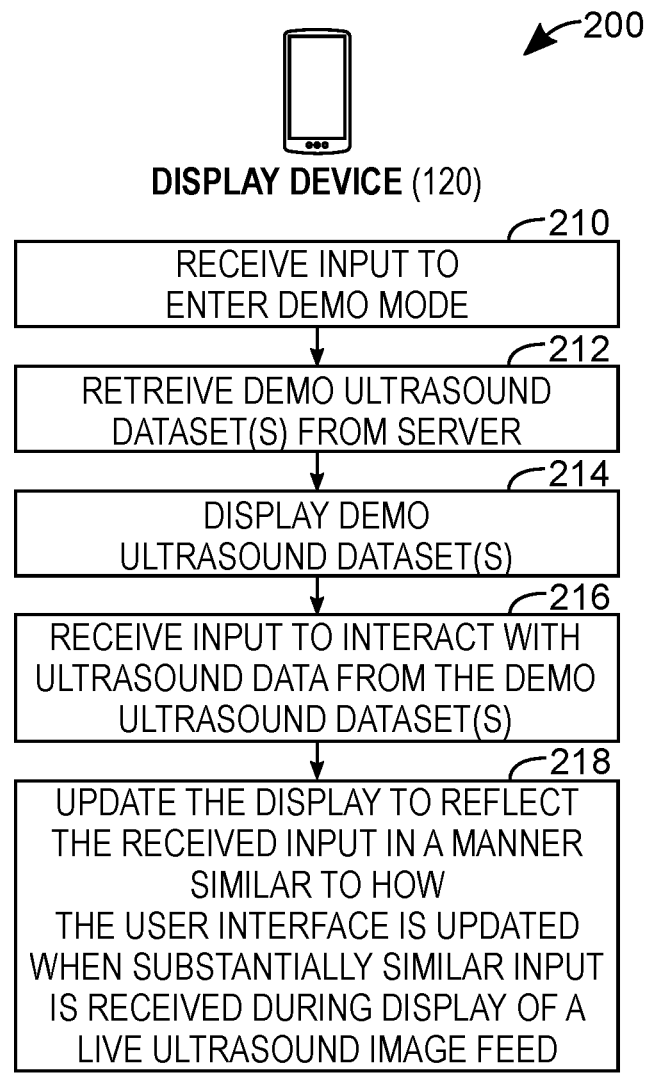
FIG. 2 is a flowchart for a method of providing an interactive demonstration of an ultrasound user interface, in accordance with at least one embodiment of the present invention.

Referring to FIG. 2, shown there generally as 200 is a flowchart for a method of providing an interactive demonstration of an ultrasound user interface, in accordance with at least one embodiment of the present invention. The method may be performed by the ultrasound application 170 provided on display device 120 shown in FIG. 1. In describing the acts of the method of FIG. 2, reference will also be made to various elements shown in FIG. 1 and the user interface screenshots shown in FIGS. 3 and 4.

At 210, the method involves receiving, e.g., via input component 132, an input from the user to enter a demonstration mode. For example, this may occur if a potential purchaser desires to try certain elements of the imaging experience without being in physical control of the ultrasound machine. In such case, they may download the ultrasound app 170 for an ultrasound machine.

Figure 3:
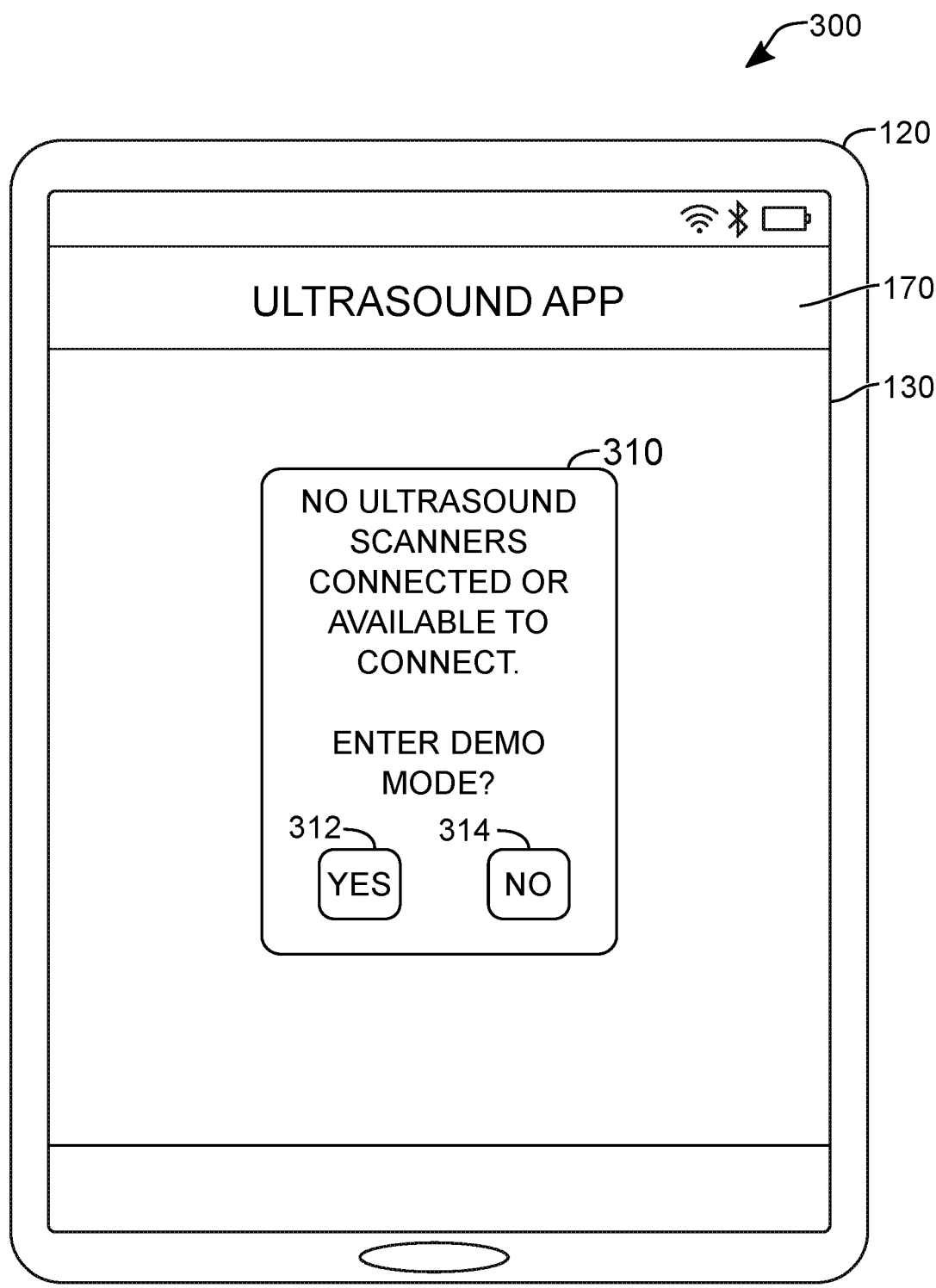
FIG. 3 shows a screenshot of an example user interface for initiating a demonstration mode, in accordance with at least one embodiment of the present invention.

Referring simultaneously to FIG. 3, shown there generally as 300, is a screenshot of an example user interface for initiating a demonstration mode, in accordance with at least one embodiment of the present invention. As illustrated, the ultrasound application 170 may be executing on the display device 120. The ultrasound application 170 may be configured to connect to ultrasound machines that encompass the probe portion. However, as illustrated, the application 170 may detect that no ultrasound scanners are connected or are available for connection. This may result in the message 310 being shown on the user interface of the ultrasound application 170 indicating that "No ultrasound scanners connected or available for connection."

Traditionally, not having the ultrasound machine available to connect to the ultrasound application 170 may prevent a user from having any meaningful experience with the ultrasound application 170. This may discourage users who downloaded the application from gaining more information about the user experience of the ultrasound machine (without actually procuring a physical machine), or those who downloaded the application out of curiosity.

However, with the present embodiments, a user without physical access to the ultrasound machine may nevertheless be able to interact with the ultrasound app 170 and perceive some elements of the ultrasound imaging experience. This may allow the user to obtain information about how the ultrasound machine may operate without going through the logistics of obtaining the ultrasound machine for trial use. As shown in FIG. 3, the message 310 shows that even though no scanners are connected or are available for connection, an option of entering a "demo mode" is possible. If the user selects the 'Yes' option 312, the ultrasound application 170 may enter the demo mode. If the user selects the 'No' option 314, the ultrasound application 170 may exit the message dialog.

The example message 310 shown in FIG. 3 is one example of how the ultrasound app 170 may present a user interface that may allow for entry into the "demo mode". As discussed below, in various embodiments, the demonstration mode can be activated by selecting a virtual demonstration ultrasound machine in a manner substantially similar to selecting an ultrasound imaging device that is connected via a port (e.g., if the ultrasound machine provides a wired connection) or selecting an ultrasound imaging device with which to pair and connect (e.g., if the ultrasound machine connects wirelessly). Additionally or alternatively, the demonstration mode can be activated automatically if no suitable ultrasound imaging machine is determined to be available for connection.

Referring back to FIG. 2, at 212, one or more demonstration ultrasound datasets can be retrieved from server 140. Once received at the display device 120, the one or more demonstration ultrasound datasets may be stored locally on display device 120 within memory 124 and/or image buffer 126.

At 214, the demonstration ultrasound dataset(s) may be displayed on display 130 of display device 120 in a manner substantially similar to how a live ultrasound data stream is displayed if an ultrasound imaging machine was connected and acquiring images.

In some embodiments, the demonstration ultrasound dataset may be a series of one or more pre-scan converted ultrasound images. When the pre-scan converted images of the demonstration ultrasound dataset is displayed, they may be processed in a manner substantially similar to how ultrasound image data received directly from an ultrasound imaging machine is processed. For example, the pre-scan converted images may be scan converted. As will be understood by a person skilled in the art, scan conversion transforms image data in a manner that allows for it to be displayed in a form that is more suitable for human visual consumption. For example, this may involve converting the image data from the data space (e.g. polar coordinate form) to the display space (e.g. Cartesian coordinate form). Scan conversion is one of the actions that renders the image data suitable for display.

In some embodiments, the demonstration ultrasound dataset may be processed to display the various images in the demonstration ultrasound dataset as if it was a continuous image stream. This may mimic the live ultrasound image feed generated by an actual physical ultrasound scanner. Since the demonstration ultrasound dataset is finite and contains a limited number of image frames, the display of the demonstration ultrasound dataset may loop to provide a continuous display of images. In some embodiments, after the final image frame is displayed, the ultrasound dataset may be displayed in reverse (e.g., starting from the last image frame and playing sequentially back to the first frame). This may allow for the display of the ultrasound images in the demonstration ultrasound dataset to appear less jagged and abrupt than if the display of the ultrasound images in the demonstration ultrasound dataset looped from the last frame back to the first frame.

At 216, input may be received to interact with ultrasound data from the demonstration ultrasound dataset(s). For example, in cases where the input component 132 includes a touchscreen interface, the input may involve the pressing of buttons and/or the receipt of touch gestures on the touchscreen interface.

At 218, the display of the demonstration ultrasound dataset can be updated to reflect the input in a manner similar to how the user interface is updated when substantially similar input is received during display of a live ultrasound image feed (e.g., as would be received from an ultrasound scanner if it were communicably connected to the display device 120).

Figure 4A:
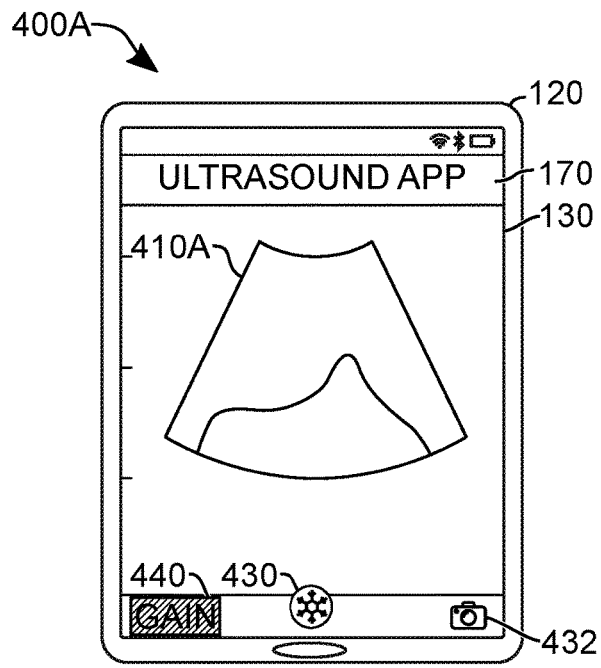
FIGS. 4A-4D show a sequence of user interface interactions of the demonstration mode, in accordance with at least one embodiment of the present invention.

Referring to FIGS. 4A-4D, shown there generally as 400A-400D are a sequence of user interface interactions of the demonstration mode, in accordance with at least one embodiment of the present invention. Referring first to FIG. 4A, the display 410A of ultrasound data from a demonstration ultrasound dataset is being displayed on the display 130 of the display device 120. As illustrated, the ultrasound app 170 may generally provide a user interface with controls that can manipulate the acquiring and viewing of ultrasound mages. For example, in the context of a live ultrasound image feed from an ultrasound scanner, these controls may include a "freeze" control 430 that stops acquisition of the ultrasound image feed, a "capture" control 432 that allows for saving/storage of an image being displayed, and a "gain" button 440 which may be activated to change the gain settings of the ultrasound image data being acquired.

FIGS. 4A-4D show operation of the ultrasound app 170 in a demonstration mode in which some of the functions typically available during live scanning are controllable and others are non-controllable. For example, in one embodiment, since the demonstration mode of the ultrasound 170 is displaying ultrasound images that have already been acquired, certain controls that allow for modification of image acquisition parameters may be non-controllable because those parameters cannot be changed. As illustrated in FIG. 4, the "gain" button 440 may traditionally be accessible during live imaging to modify the gain on various aspects of a live ultrasound image feed being acquired. However, since it may not be possible to change these parameters with the demonstration ultrasound dataset, this non-controllable control may be distinguished graphically (e.g., shown in a different colour or 'greyed-out'). In FIGS. 4A-4D, this is shown with the button 440 having hatched shading, For the controllable functions that can be performed on the demonstration ultrasound dataset (e.g., the "freeze" control 430 and the "capture" control 432 shown in FIGS. 4A-4D), these controls are shown in their regular visual appearance and can be accessible when the ultrasound app 170 is operating in the demonstration mode. In this manner, the user interface displayed by the ultrasound app 170 during the demonstration mode may be considered substantially similar to the user interface shown by the ultrasound app 170 when an ultrasound imaging machine is connected and supplying ultrasound imaging data.

Figure 4B:
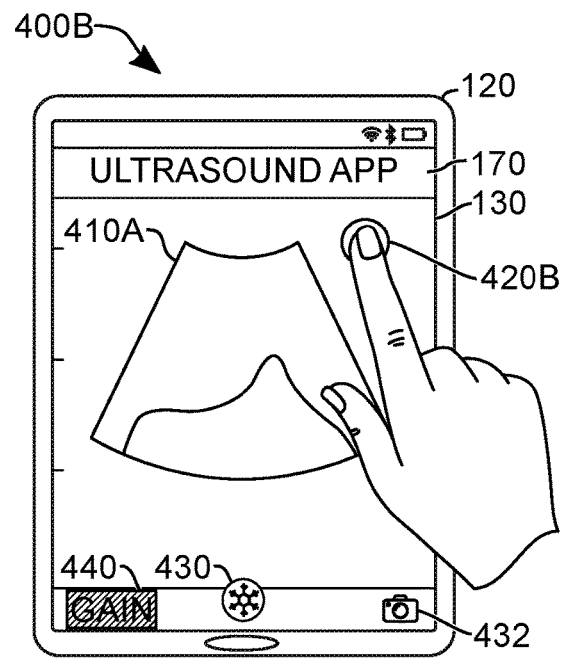
Figure 4C:
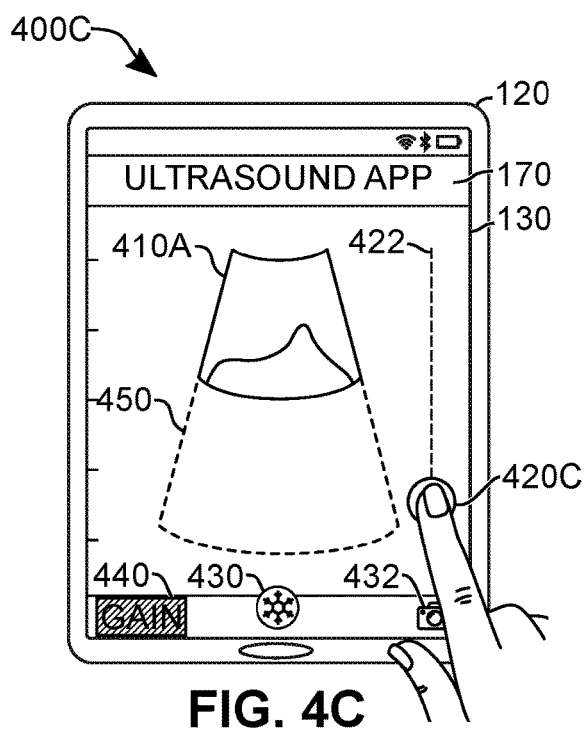
Figure 4D:
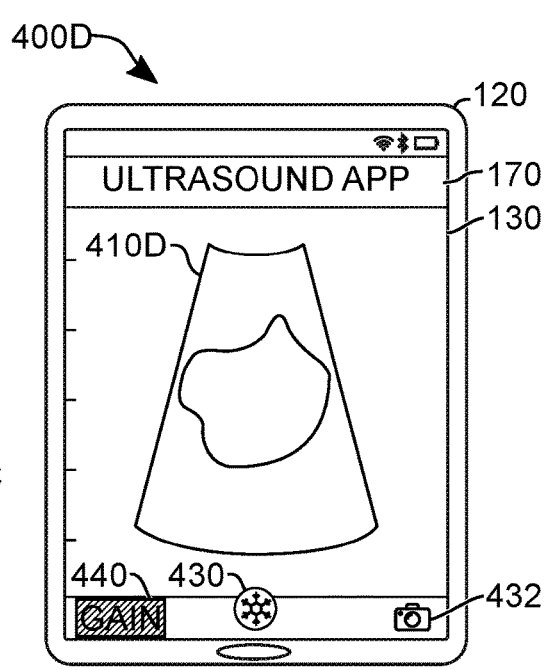

Referring to FIG. 4B, shown there generally as 400B is a screenshot of the user interface of the ultrasound app 170 at a point in time subsequent to FIG. 4A. Some of the user interface controls that can be manipulated in the user interface of the ultrasound app 170 may include a touch gesture (e.g., a drag gesture). FIGS. 4B-4D show a sample input of a drag gesture at three successive points in time for increasing imaging depth during operation of the demonstration mode of the ultrasound app 170. As shown in FIG. 4B, the user may initiate contact with the touchscreen at 420B while the ultrasound image 410A from the demonstration ultrasound dataset is being displayed.

Referring to FIG. 4C, shown there generally as 400C is a screenshot of the user interface of the ultrasound app 170 subsequent to FIG. 4B. FIG. 4C shows generally an example transitional view of the ultrasound image 410A when adjusting imaging depth. As the touch gesture moves from the initial touch point at 422 to the new touchpoint at 420C, the user interface may display a transitional view during the continuous contact that provides previews 450 of the image depth being adjusted.

Referring to FIG. 4D, shown there generally as 400D is a screenshot of the user interface of the ultrasound app 170 subsequent to FIG. 4C. Upon termination of the touch gesture at the point 420C shown in FIG. 4C, the user interface of the ultrasound app 170 may be updated to reflect the imaging depth of the preview 450. As shown in FIG. 4D, the user interface of the ultrasound app 170 may be updated to show ultrasound images 410D with increased imaging depth.

The updating of the ultrasound image 410A with a first depth to another ultrasound image 410D with a second depth may be performed in various ways. For example, in one embodiment, the demo ultrasound dataset may be configured to be acquired at a relatively large imaging depth for the demo scanner (e.g., >25 centimeters for a curvilinear scanner or 7-10 centimeters for a linear scanner). Then, when ultrasound images from these relatively deep imaging depths are displayed and imaging depth is modified via the user interface or other input, the ultrasound app 170 may perform a digital zoom on the ultrasound images being displayed when the imaging depth is decreased (e.g., to only display the shallow portion of the ultrasound images in the demo ultrasound dataset). Correspondingly, when the imaging depth is increased, the ultrasound app 170 may reduce the zoom level to reveal more of the ultrasound images from the demo ultrasound set (e.g., restore viewing of at least some of the deeper view of the images in the demo ultrasound dataset).

Alternatively, in some embodiments, instead of displaying and allowing for navigation of a demo ultrasound dataset that is acquired at a single imaging depth, the demo mode may be configured to navigate multiple demo ultrasound datasets, each acquired at different respective imaging depths. For example, if a demo mode is being provided for an ultrasound machine with a convex transducer that can image up to depths of 30 centimeters, it may be possible, in one example embodiment, to provide three (3) demonstration ultrasound datasets that are optimized for viewing three different imaging depth ranges: e.g., 1-10 cm imaging depth, 10-20 cm imaging depth, and 20-30 cm imaging depth.

Figure 5:
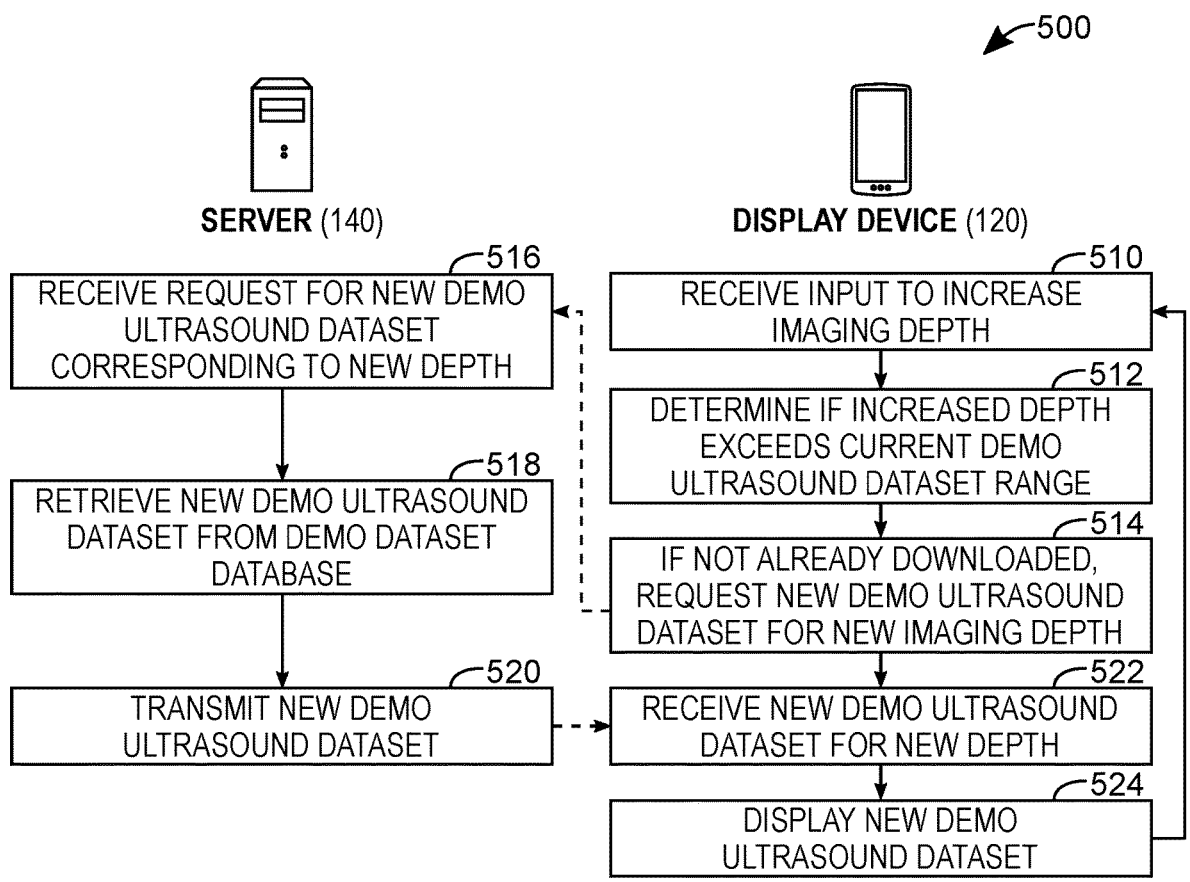
FIG. 5 shows a flowchart for a method of retrieving ultrasound demonstration data from a server, in accordance with at least one embodiment of the present invention.
Figure 6:
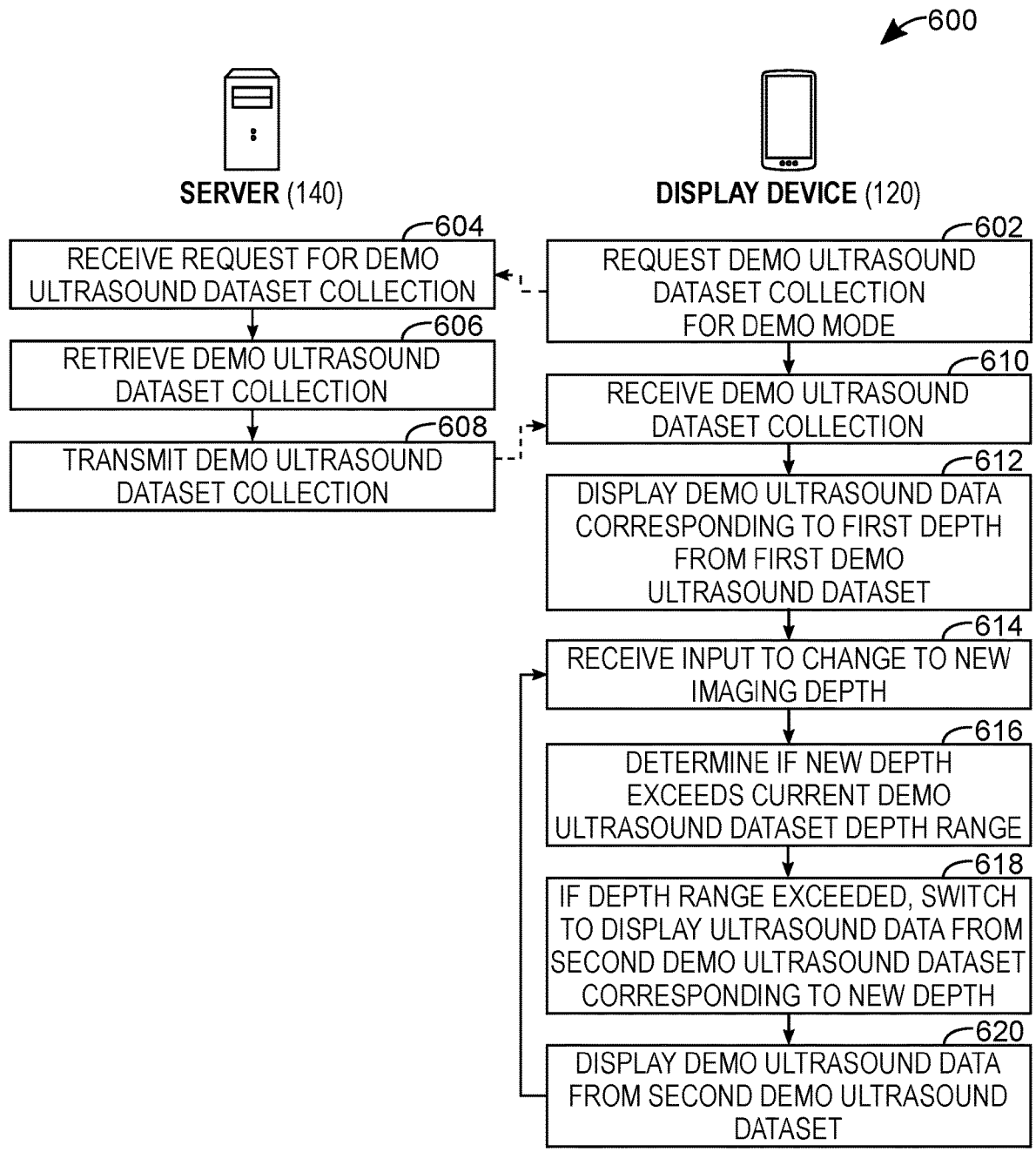
FIG. 6 shows another flowchart for a method of retrieving ultrasound demonstration data from a server, in accordance with at least one embodiment of the present invention.

Embodiments where multiple demonstration ultrasound datasets are navigated are discussed with respect to FIGS. 5 and 6. In both FIGS. 5 and 6, the demo mode of the ultrasound app 170 may switch amongst different demo ultrasound datasets acquired at different imaging depths based on the imaging depth received as input in the demo user interface. In the embodiment of FIG. 5, the additional demo ultrasound datasets are retrieved on an on-demand, as-needed basis. In the embodiment of FIG. 6, an entire ultrasound dataset collection (having multiple demo ultrasound datasets) is downloaded in advance, and the demo mode of the ultrasound app 170 is configured to switch amongst the different demo ultrasound datasets based on received user input in the demo mode.

Referring to FIG. 5, shown there generally as 500 is a flowchart for a method of retrieving ultrasound demonstration data from a server, in accordance with at least one embodiment of the present invention. In referring to the method of FIG. 5, reference may also be made to the components shown in FIG. 1 and the user interface screenshots shown in FIG. 4. In the embodiment of FIG. 5, prior to a first act 510 being performed, the display device 120 may already be operating in the demo mode and displaying ultrasound images from an already-retrieved first demo ultrasound dataset containing images acquired at a first imaging depth.

At 510, input may be received to change imaging depth. For example, the touch gesture of FIGS. 4B-4C may be used to provide input indicating a change of imaging depth.

At 512, the display device 120 may determine whether the imaging depth change requested in act 510 exceeds the depth range of the current demonstration ultrasound dataset. For example, upon the release of the touch gesture to input an imaging depth as shown in FIG. 4C, the display device 120 may determine that the increased imaging depth inputted by the touch gesture exceeds (e.g., is either less than or greater than) the depth range of the ultrasound images in the first (current) demonstration ultrasound dataset being displayed. The display device 120 may then determine if a second demonstration ultrasound dataset corresponding to the inputted image depth has already been downloaded. If so, the display device 120 may switch to displaying ultrasound images from that second demonstration ultrasound dataset.

At 514, if that second demonstration ultrasound dataset has not already been downloaded, the display device 120 may transmit a request to server 140 for a new demonstration ultrasound dataset for the imaging depth inputted at act 510. The request may be handled by communication interface 128 of display device 120.

At 516, the server 140 receives the request for the demonstration ultrasound dataset. In some embodiments, the demo service 142 of the server 140 may provide an Application Programming Interface (API) that is configured to listen for requests such as would be transmitted by the display device 120 (e.g., as a result of act 514).

At 518, the demo service 142 at the server 140 may then retrieve a second (new) demonstration ultrasound dataset from the ultrasound dataset database 144. The retrieved second (new) demonstration ultrasound dataset may be transmitted from the server 140 to the display device 120 (act 520).

At 522, the second (new) demonstration ultrasound dataset corresponding to the new imaging depth inputted may be received by display device 120. The demonstration dataset may be stored in memory 124 and/or image buffer 126 of display device 120. The ultrasound application 170 may then display ultrasound images from the second (new) demo ultrasound dataset that corresponds to the new imaging depth (act 524). The method may then loop back to act 510 to receive additional input for modifying imaging depth.

Referring to FIG. 6, shown there generally as 600 is another flowchart for a method of retrieving ultrasound demonstrate data from a server, in accordance with at least one embodiment of the present invention. In referring to the method of FIG. 6, reference may also be made to the components shown in FIG. 1. As noted above, FIG. 6 shows a different method of how multiple demo ultrasound datasets for different imaging depths can be retrieved from a server 140. Similar to FIG. 5, the acts shown as being performed by the display device 120 in FIG. 6 may generally be performed by the ultrasound app 170 executing on a display device 120. Likewise, the acts shown as being performed by the server 140 may generally be performed by the demo service 142. In the embodiment of FIG. 6, prior to a first act 602 being performed, the display device 120 may receive input to enter a demo mode of the ultrasound app 170.

At 602, the display device 120 may transmit a request for a demonstration ultrasound dataset collection to server 140. This request may be received at the server 140 (act 604).

At 606, the server 140 may retrieve the demonstration ultrasound dataset collection from the demonstration ultrasound dataset database 144. The collection may include multiple demonstration ultrasound datasets, each acquired at different imaging depths. The retrieved demonstration ultrasound dataset collection may be transmitted to display device 120 (act 608), and received at the display device (act 610). Once received, the display device 120 may store the demonstration ultrasound dataset collection within memory 124 and/or within image buffer 126.

At 612, the display device 120 may select one of the demonstration ultrasound datasets from the received collection for displaying. For example, the demonstration ultrasound dataset selected in this instance may be based on a first default depth and/or the last imaging depth viewed during the last use of the demo mode. As noted, various processing acts may be required to process the data within a demonstration ultrasound dataset for display. For example, the data within the demonstration ultrasound dataset may be pre-scan converted data and the one or more processing acts may include scan conversion.

At 614, the display device 120 may receive input (e.g., via input component 132 or sensor 138) to change imaging depth. The input may include using gestures on a touchscreen (e.g., as shown in FIGS. 4B-4C), pressing buttons, or giving voice commands.

At 616, the display device 120 may determine if the requested depth change exceeds the depth range of the current demonstration ultrasound dataset being displayed.

At 618, if the requested imaging depth exceeds the depth range of the current demonstration ultrasound dataset in act 616, the display device 120 may switch to display ultrasound data from a second demonstration ultrasound dataset corresponding to the new depth. The display device 120 may then display demonstration ultrasound data from the second demonstration ultrasound dataset (act 620).

The method may then loop back to act 614 as new input to change imaging depth is received. This may allow switching amongst the different demonstration ultrasound datasets of the collection received at act 610, based on the inputted imaging depth.

Unlike the embodiment of FIG. 5 where demo ultrasound datasets for a given imaging depth are retrieved on-demand based on inputted image depth, the embodiment of FIG. 6 downloads an entire collection of demo ultrasound datasets for all available imaging depths and switches amongst them when new imaging depths are inputted. The embodiment of FIG. 5 may provide a smaller initial download size to allow for the demo mode of the ultrasound app 170 to begin displaying images more quickly upon initial execution. However, the user interface may potentially experience a slight lag the first time the demo ultrasound dataset for a given imaging depth is requested. In contrast, the user interface in the embodiment of FIG. 6 may experience a slightly slower initial start-up time to allow for the entire demo ultrasound dataset collection to be downloaded. However, it may not be as likely to experience the lag upon changing of imaging depths since no live downloading of demo ultrasound datasets would be performed.

In a further embodiment, to provide both a quick initial start-up experience and reduce the potential for experiencing a lag when a given demo ultrasound dataset is retrieved for the first time, the ultrasound app 170 may be configured to retrieve the demo ultrasound datasets of a collection in a staged manner. For example, a first demo ultrasound dataset for a first default imaging depth may be retrieved. Once retrieved, the ultrasound app 170 may begin processing and displaying the ultrasound images in the first demo ultrasound dataset. The ultrasound app 170 may then start downloading the remaining demo ultrasound datasets in the background. If/when input is received to change imaging depth, the ultrasound app 170 may then switch to the already-downloaded demo ultrasound dataset for the inputted imaging depth. This may avoid the potential lag that may be experienced if downloading of that demo ultrasound dataset was only performed upon input of the imaging depth.

In the embodiments discussed above, demo ultrasound datasets may only be downloaded when a demo mode of the ultrasound app 170 is entered into. This may allow the size of the ultrasound app 170 to be smaller because the demo ultrasound datasets are only sent to users who desire to operate in the demo mode. However, in various embodiments, various demo ultrasound datasets may be included in the data of the ultrasound app 170 itself.

The discussion above with regards to FIGS. 5 and 6 has generally been with respect to providing different demonstration ultrasound datasets for different imaging depths so that when a new imaging depth is inputted in the demo mode of the ultrasound app 170, the app 170 may switch to a demonstration ultrasound dataset that provides the best sample images at the selected depth. However, in various embodiments, the providing of different demonstration ultrasound datasets may not be limited just to the imaging depth parameters.

For example, in some embodiments, it may be possible to provide different demonstration ultrasound datasets for different settings of another imaging parameter that, if the display device 120 was connected to an ultrasound machine, would typically require a sending of a signal to the ultrasound machine to modify an imaging parameter.

For example, in the discussion of FIGS. 4A-4D above, it was noted that some user interface controls typically provided on the ultrasound app 170 when connected to an ultrasound machine may be controllable and other user interface controls may be non-controllable. As illustrated in FIGS. 4A-4D, a button for modifying 'gain' settings may be greyed-out since it may not be possible to change gain imaging parameters with the ultrasound image data of a demo ultrasound dataset that was already acquired with fixed gain settings.

However, in some embodiments, it may be possible to convert any non-controllable functions to controllable functions by providing additional demo ultrasound datasets that correspond to different settings for a given imaging parameter. For example, it may be possible to have the 'gain' settings be controllable in the demo mode by providing different demonstration ultrasound datasets for different gain settings. When input to modify gain is then received by the ultrasound app 170, the ultrasound app 170 may switch between different demonstration ultrasound datasets that best reflect the gain setting inputted in the demo mode. This method of providing different demonstration ultrasound datasets may be applicable for any single or combination of imaging parameters that would typically require sending of a signal to the ultrasound machine to modify its operation. For example, the imaging parameters for which different demonstration ultrasound datasets may be provided include: frequency (e.g., demonstration ultrasound datasets for resolution, general, and penetration settings), focus position, focal zones, and Time Gain Compensation (TGC).

In various embodiments, if multiple imaging parameters are made controllable in the demo mode, it is possible that different demonstration ultrasound datasets are provided for different permutations of the settings for the multiple imaging parameters. For example, if imaging depth and frequency are made controllable, different demonstration ultrasound datasets may be provided for different permutations of these settings (e.g., if imaging depth has 3 possible settings of shallow, medium, and deep; and frequency has 3 possible settings of low, medium, and high frequencies, then there may potentially be 9 demonstration ultrasound datasets for all the various combinations of these settings).

While the embodiments discussed herein have generally referred to demonstration ultrasound datasets that consist of B-mode image data, in various embodiments, the demonstration ultrasound datasets may also include data acquired from various imaging modes, including: motion-mode (M-mode), color Doppler, continuous wave (CW) Doppler, pulsed wave (PW) Doppler, pulse inversion mode, and harmonic mode; or combinations of two or more of these modes. For example, one or more demonstration ultrasound datasets may be provided that contain color flow imaging data, so that a user can adjust the position and size of the region of interest on demo B-mode images to see the corresponding color flow imaging data. In another example, one or more demonstration ultrasound datasets may be provided for different M-mode acquisition lines or pulse wave Doppler regions of interest on demo B-mode images. Then, in the demo mode, a user may try imaging in one of those modes, and the user interface may 'snap' to the line or ROI for which the M-mode line or pulse wave Doppler data was acquired to provide a viewing of the user interface in that mode. This 'snapping' of the user interface in the demo mode may be necessary for these latter examples because it can be difficult to acquire M-mode signals or pulse wave Doppler signals across an entire image.

Figure 7:
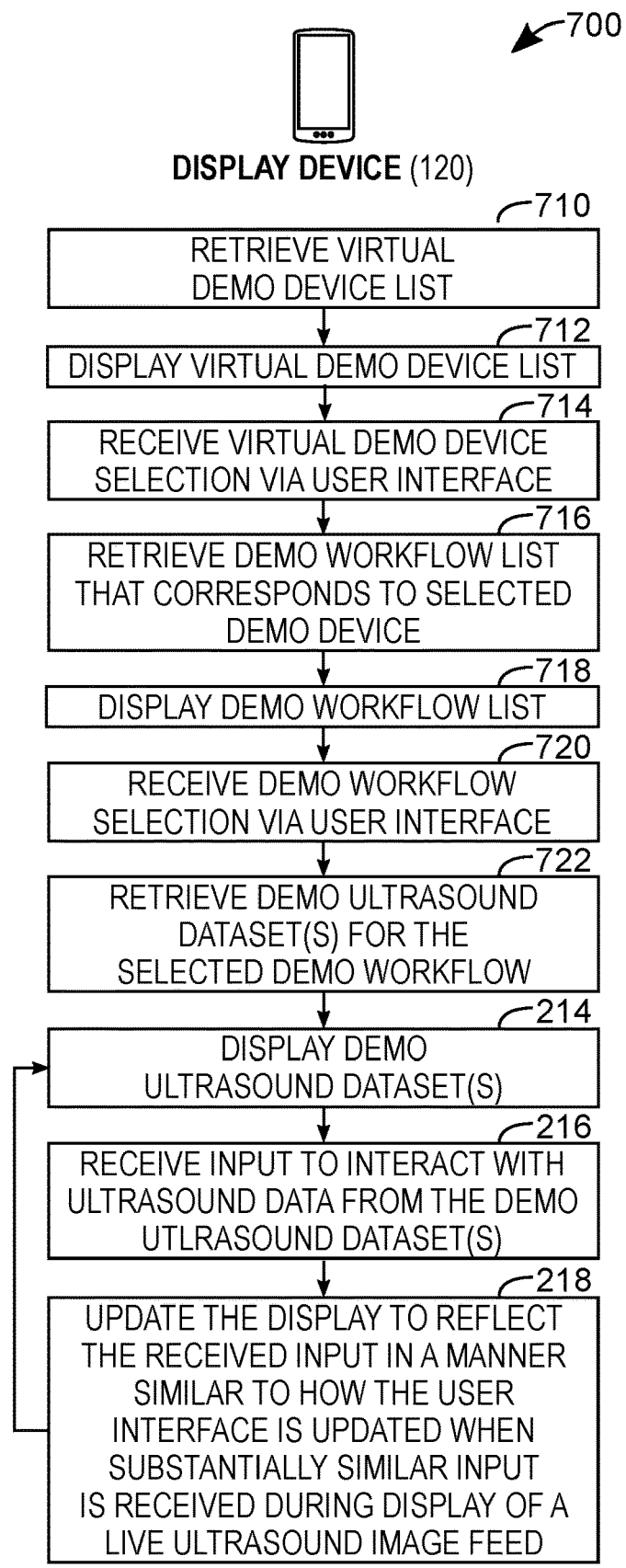
FIG. 7 shows a flowchart for a method of providing an interactive demonstration of an ultrasound user interface via virtual demonstration imaging devices and associated demonstration workflows, in accordance with at least one embodiment of the present invention.

Referring to FIG. 7, shown there generally as 700 is a flowchart for a method of demonstrating operation of an ultrasound imaging system via virtual imaging devices and associated demonstration workflows, in accordance with at least one embodiment of the present invention. In referring to the method of FIG. 7, reference may also be made to the components shown in FIG. 1 and the example user interface screenshots shown in FIGS. 8 and 9. The acts shown as being performed by the display device 120 in FIG. 7 may generally be performed by the ultrasound app 170 executing on a display device 120.

At 710, the display device 120 may retrieve a virtual demo device list. In various embodiments, the virtual demo device list may be stored locally in the memory 124 of display device 120. Additionally or alternatively, the virtual demo device list may also be retrieved from server 140 (e.g., via demo service 142). The display device 120 may display the virtual demo ultrasound device list having of one or more virtual demo ultrasound imaging devices (act 712).

Figure 8:
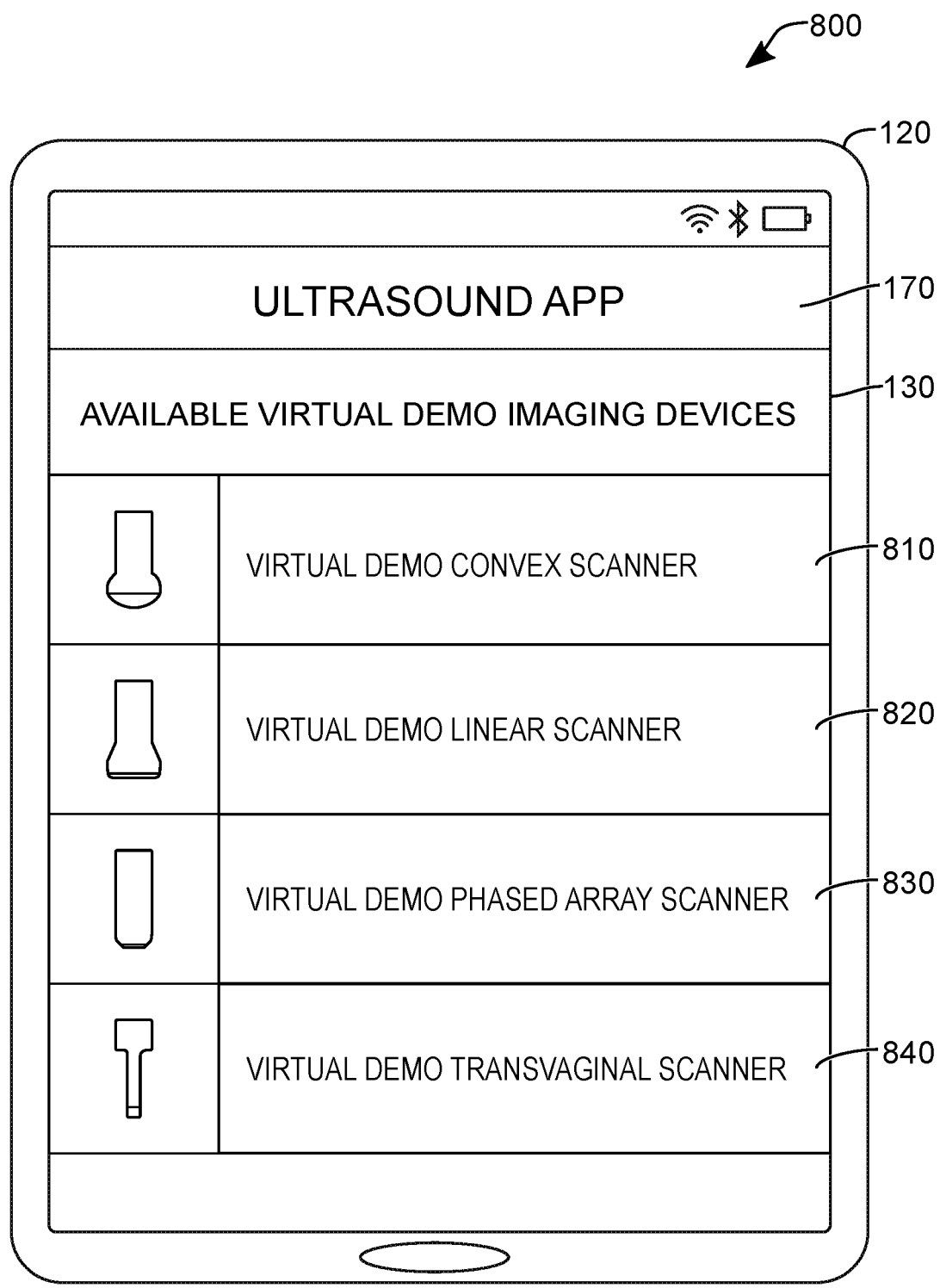
FIG. 8 shows a screenshot of an example user interface for selecting a virtual demonstration imaging device, in accordance with at least one embodiment of the present invention.

Referring simultaneously to FIG. 8, shown there generally as 800 is a screenshot of an example user interface for selecting a virtual imaging device, in accordance with at least one embodiment of the present invention. The ultrasound app 170 may configure display 130 of the display device 120 to display the list of available virtual demonstration ultrasound imaging devices. As illustrated, the available virtual demonstration ultrasound imaging devices are shown in a list labeled "Available virtual demo imaging devices". Four demonstration devices are available to be selected: a "virtual demo convex scanner" 810, a "virtual demo linear scanner" 820, a "virtual demo phased array scanner" 830, and a "virtual demo transvaginal scanner" 840. In the illustrated embodiment, the virtual demonstration ultrasound imaging devices are shown in a separate list just for virtual demo imaging devices. However, additionally or alternatively, the demonstration ultrasound devices can be listed along with ultrasound imaging devices that are within physical proximity and available for pairing and connection.

In some embodiments, the virtual demonstration imaging device list may include an indication (not shown in FIG. 8) of whether a given displayed device requires download of additional data. For example, this may be the case if a given virtual demonstration ultrasound imaging device is available for selection, but the ultrasound app 170 does not have the corresponding data to allow for its operation (e.g., the necessary demonstration ultrasound datasets) stored in memory 124 on the multi-use electronic display device 102. For example, to provide this indication, list items may be colored differently and/or be configured to include a graphic element that indicates whether it is available or not.

As discussed above in relation to FIG. 3, one example way of entering a "demo mode" of the ultrasound app 170 may be via a message box that pops up if no ultrasound scanners are detected as being connected or available for connection. However, FIG. 8 shows an additional or alternative method of entering the demo mode by selecting a virtual demonstration ultrasound machine in a manner substantially similar to how an actual physical ultrasound imaging device can be selected in the ultrasound app 170.

In an embodiment where the ultrasound app 170 allows for pairing and connection to multiple nearby ultrasound machines (e.g., if the ultrasound app 170 connects with ultrasound machines wirelessly), entry into the demo mode via this method may allow a potential user to become familiarized with the ultrasound machine selection process. Also, since ultrasound scanners having different transducer geometries may have demo ultrasound datasets and/or user interface components, providing entry into the demo mode by way of the device selection screen may allow different virtual demo ultrasound machines having different respective transducer geometries to be tried and demonstrated.

Referring back to FIG. 7, at 714, input may be received at the display device 120 (e.g., via input component 132) to select a virtual demo ultrasound imaging device. For example, touch input may be received via the user interface of FIG. 8 to select one of the virtual demonstration ultrasound imaging devices.

At 716, the display device 120 may retrieve a demo workflow list that is available for the ultrasound demonstration device selected in act 714. In various embodiments, the demo workflow list may be stored locally in memory 124 of display device 120 or retrieved from server 140. The display device 120 may display the demo workflow list on the display 130 (act 718).

In some embodiments, the list of demonstration workflows may also include workflows with demonstration ultrasound dataset(s) that correspond to specific pathologies. For example, there may be demonstration workflows that correspond to a normal cardiac scan, a cardiac scan with cardiac tamponade and a cardiac scan with enlarged walls. These demonstration workflows may be provided as separate list items or as a selectable subcategory within the base workflow (e.g., cardiac).

Figure 9:
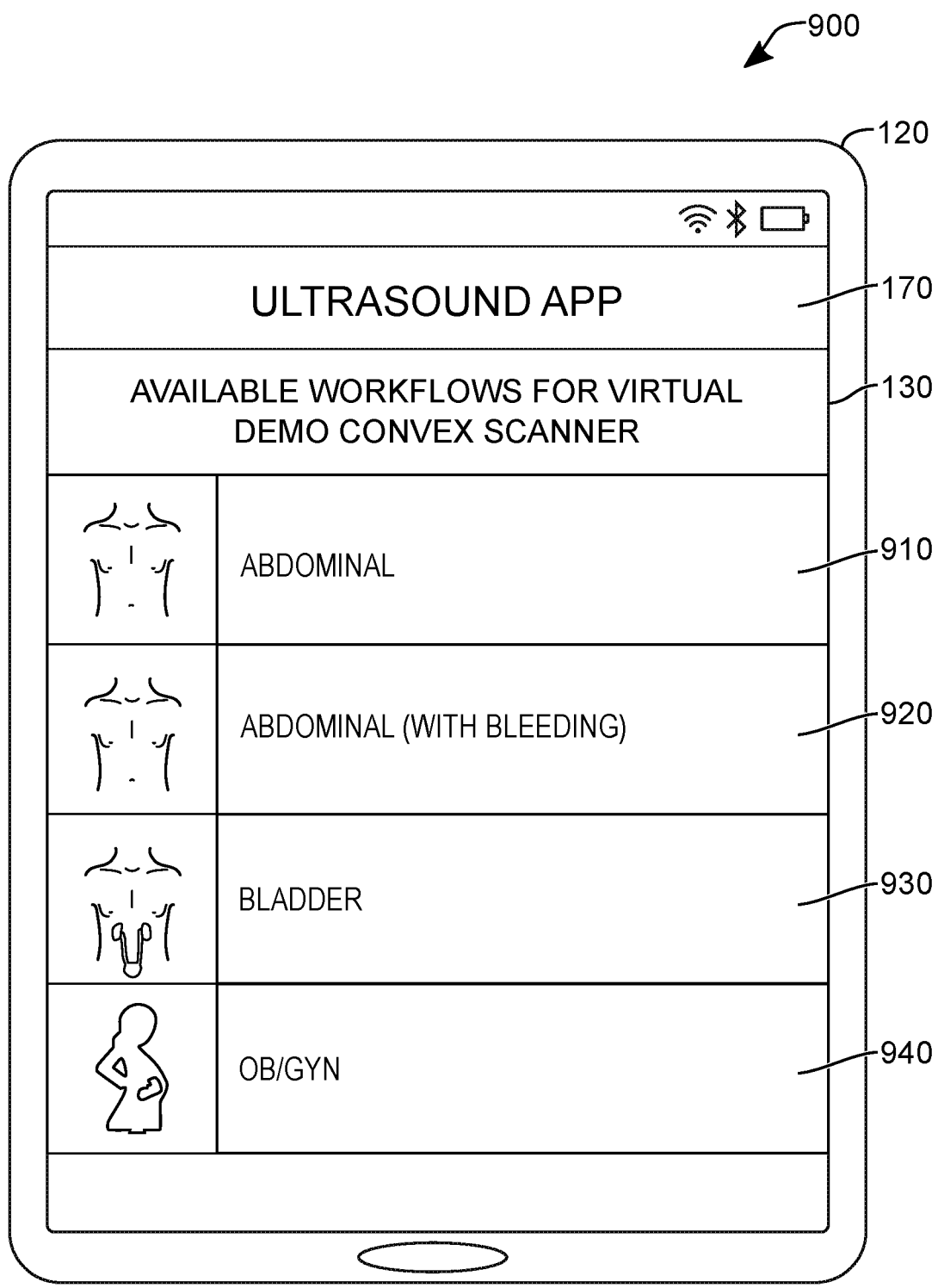
FIG. 9 shows a screenshot of an example user interface for selecting a demonstration workflow associated with a virtual demonstration imaging device, in accordance with at least one embodiment of the present invention.

Referring simultaneously to FIG. 9, shown there generally as 900 is a screenshot of an example user interface for selecting a demonstration workflow associated with a virtual demo imaging device, in accordance with at least one embodiment of the present invention. The ultrasound app 170 may configure display 130 of the display device 120 to display the demo workflow list for a virtual demo ultrasound imaging device selected in the user interface of FIG. 8. In the illustrated embodiment, a "virtual demo convex scanner" may have been selected in the user interface of FIG. 8. As a result, the user interface of FIG. 9 may be configured to display "Available workflows(s) for virtual demo convex scanner". As shown, these workflows include: "abdominal" 910, "abdominal (with bleeding)" 920, "bladder" 930, and obstetrics/gynaecology ("OB/GYN") 940.

In some embodiments, the list of demonstration workflows may include an indication for whether a particular demonstration workflow device is already stored in memory 124 of display device 120 or whether it needs to be retrieved from server 140. For example, list items may be colored differently, or include a graphic element that indicates whether it is available or not.

Referring back to FIG. 7, at 720, the display device 120 may receive input (e.g., via the input component 132) to select a demonstration ultrasound workflow. Based on the selected demonstration workflow, the display device 120 may retrieve demo ultrasound dataset(s) for the selected demo workflow (act 722). In various embodiments, the demo ultrasound dataset(s) may already be stored locally in memory 124 of display device 120 or retrieved from server 140 (in the manner discussed above).

After selecting a demonstration workflow, the display device 120 may operate in a manner substantially similar to how the ultrasound app 170 operates when a physical ultrasound imaging device is connected. For example, display device 120 may show a series of screens that include input of patient information, and/or freezing or storing an ultrasound image, and/or the input of measurements or annotations.

As will be apparent to a person skilled in the art, ultrasound scanners with different probe geometries and/or transducer configurations may typically be associated with different types of ultrasound workflows related to the type of medical examination each type of scanner is typically used for. For example, as shown in FIG. 8, a convex scanner may typically be used to perform abdominal, bladder, and/or obstetrics/gynaecology examinations. In another example, a linear scanner may be used to perform vascular access and/or musculoskeletal (MSK) examinations. For the different types of examinations, the ultrasound app 170 may typically be configured to provide a workflow that includes certain presets, user interface features, and/or software packages (e.g., certain types of indications, measurements and/or annotations may be applicable only to a type of medical examination). By providing the ability to experience the workflows specific to a given scanner type, the demo mode of the ultrasound app 170 may provide the ability to experience (and be provided a demonstration of) these aspects of how a given scanner type is used.

Referring still to FIG. 7, at 214, the display device 120 may display the demo ultrasound dataset(s) retrieved on display 130. Input may then be received via the user interface of the demo mode of the application 170 to interact with the ultrasound data from the demonstration ultrasound dataset(s) (act 216). Upon receipt of input, at act 218, the method may proceed to update the display to reflect the received input in a manner similar to how the user interface is updated when substantially similar input is received during display of a live ultrasound image feed. Acts 214-218 of FIG. 7 may generally be performed in a manner similar to the corresponding acts discussed above in relation to FIG. 2.

Figure 10:
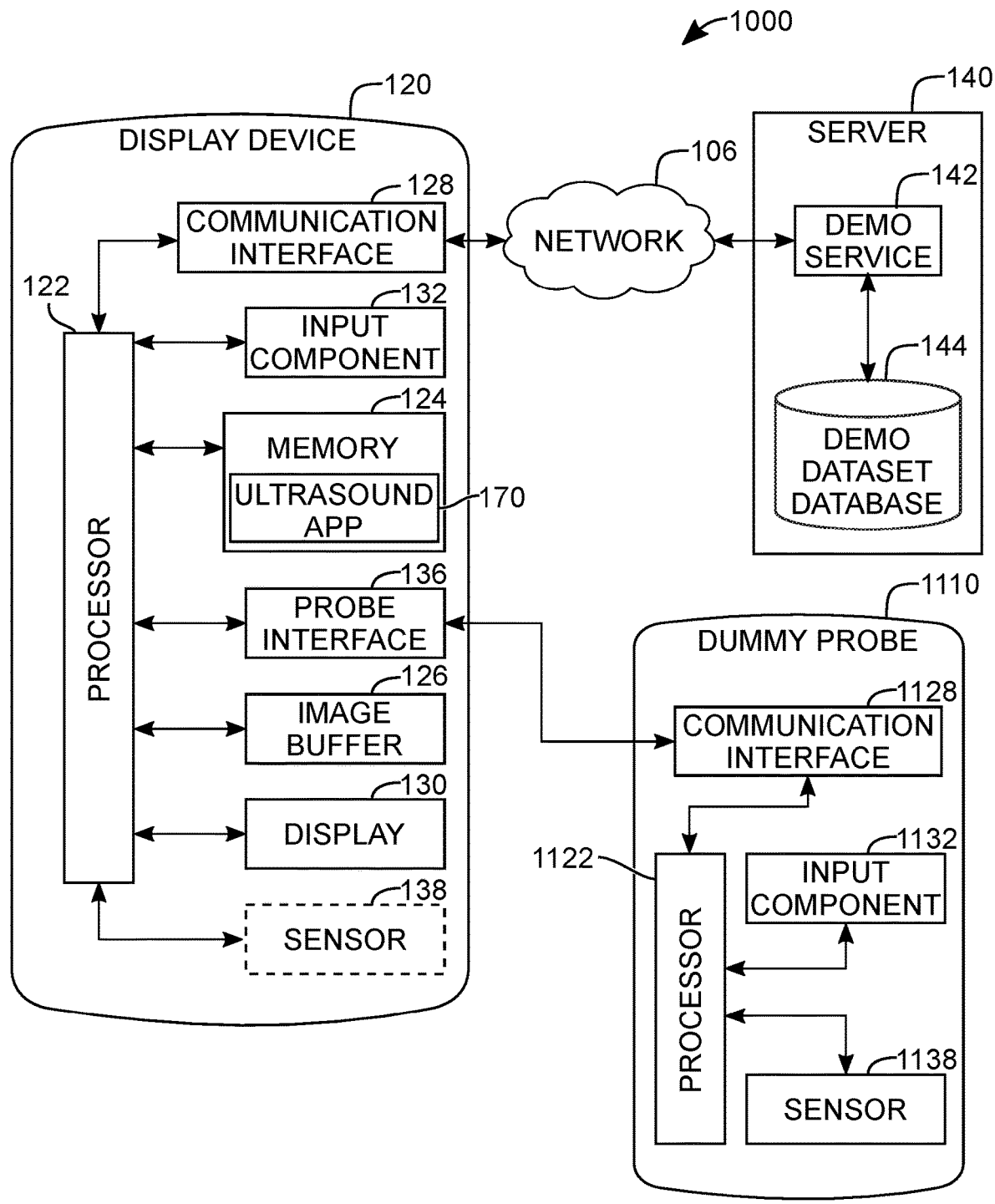
FIG. 10 is a functional block diagram of an alternative embodiment of a system for providing an interactive demonstration of an ultrasound user interface, in accordance with at least one embodiment of the present invention.

Referring to FIG. 10, shown there generally as 1000 is a functional block diagram of an alternative embodiment of a system for providing an interactive demonstration of an ultrasound user interface, in accordance with at least one embodiment of the present invention. The various devices and elements of the system 1000 is similar to that shown in FIG. 1, except that a dummy probe 1110 is also provided. The dummy probe 1110 can be communicatively connected to display device 120 via probe interface 136.

Dummy probe 1110 may be a second display device such as a commercially available smartphone, tablet computer, or laptop computer, or a custom-built table computer. Additionally or alternatively, dummy probe 1110 may be a custom-built device that has a subset of the features of the ultrasound imaging machine. For example, dummy probe 1110 may have a shape and size that is substantially similar to the shape and size of an ultrasound imaging device. The dummy probe 1110 may include a minimal set of electronics for reduced cost, without the functionality to acquire ultrasound imaging data.

Dummy probe 1110 may include a communication interface 1128, processor 1122, input component 1132, and sensor 1138. Communication interface 1128 may be configured to communicate with display device 120. As discussed above with reference to FIG. 1, the connection between dummy probe 1110 and display device 120 may be via a data port (e.g., Universal Serial Bus (USB), Lightning™ or other suitable data port) and/or via suitable wireless communication protocol(s) (e.g., Bluetooth™, Wi-Fi™, and any other similar or future-developed wireless communication protocol).

Input component 1132 may be substantially similar to the input component 132 of display device 120 and include, for example, a touchscreen. Alternatively or in addition, input component 1132 may include inputs typically found on an ultrasound imaging device, such as buttons to perform a freeze function or modify depth and/or gain.

Sensor 1138 may be similar to sensor 138 of display device 120 and include, for example, an inertial measurement sensor, accelerometer, gyroscope, and/or any other well known or future developed sensor for measuring position and/or orientation.

Referring simultaneously back to FIG. 2, when the ultrasound app 170 is operating in demo mode, input received by dummy probe 1110 may be transmitted to display device 120 and used as input in act 216 to interact with ultrasound data from the demo ultrasound dataset(s). For example, the orientation of dummy probe 1110 may be measured by sensor 1138 and transmitted to the display device 120 as input in act 216, then used to update the display of the ultrasound data in act 218. In an example embodiment, different demo ultrasound datasets may be tagged with different respective values of potential sensor input (e.g., yaw, pitch, roll values for a gyroscope), and when corresponding input values are determined by sensor 1138 and provided to the demo mode of the ultrasound app 170, the display device 120 may look up the suitable corresponding demo ultrasound dataset and switch to it for display.

In some embodiment, data from two or more demo ultrasound datasets may be combined to generate suitable ultrasound data to display. For example, ultrasound data from two or more demo ultrasound datasets may be interpolated in response to a physical movement of the dummy probe 1110 to provide a realistic impression of how the ultrasound images would appear if a connected ultrasound imaging machine was moved in a substantially similar movement. In some embodiments, the user may be provided with an indication (e.g., a graphical indicator on the user interface) to alert them when simulated or combined data is being displayed. In some embodiments, the user may control whether or not combined data is displayed.

The embodiments described herein provide systems and methods for enabling a user to interact with the user interface of an ultrasound system without requiring an ultrasound imaging machine to be connected. This may enable a user to test/sample the features of the ultrasound system without having to purchase or physically be in possession of the ultrasound imaging machine. This may also enable a user to learn how to use the features of the user interface of the ultrasound system.

In addition to demonstration and trial purposes, the various embodiments described herein may also be used for education and training in certain instances. For example, in some embodiments, an instructor may distribute demonstration ultrasound datasets to one or more students equipped with multi-use electronic display devices 120, but not equipped with ultrasound imaging machines. In this way, the students may learn and practise portions of the ultrasound-based medical examination that do not include acquiring images with the ultrasound imaging machine. These portions of the medical examination may include: learning how to use the graphical interface of display device 120 (including how to select a device, how to choose a workflow and/or examination type); how to enter patient information; and/or how to select indications. These users may also be exposed to how to interact with a live ultrasound image stream, including, for example, freezing the image, saving an image, creating and navigating through a cine-loop, and/or adding annotations and measurements. The portions may also include determining diagnoses based on the ultrasound images.

In various embodiments, the embodiments described herein may offer a desirable way to provide standardized testing. For example, providing a consistent ultrasound dataset between students may allow the instructor to distinguish the ability of one student from another student in relation to how they manipulate the user interface of the ultrasound application 170 (e.g., to measure and diagnose medical conditions shown in the images of a demonstration ultrasound dataset and/or having multiple users perform the same measurement on a single demonstration dataset). The present embodiments may thus allow an instructor to assess the ability students with regards to performance of these portions of a medical examination, apart from their ability to acquire the ultrasound images.

The use of demonstration ultrasound datasets is described herein. In various embodiments, demonstration ultrasound datasets may be provided by the manufacturer (e.g., to allow for demonstration of a user interface of the ultrasound app 170 without an ultrasound machine being connected). However, in some embodiments, demonstration ultrasound datasets may also be created by users of the system described herein. For example, demonstration ultrasound datasets may be created from ultrasound data acquired with a connected ultrasound imaging device when it is present. This may enable, for example, an instructor to test students on whether they can identify/measure a particular pathology present in the user-uploaded demonstration ultrasound datasets.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of providing an interactive demonstration of an ultrasound user interface, the method comprising:
a multi-use display device, that is configured to be used with an ultrasound probe that transmits and receives ultrasound energy for generating ultrasound images for display on the multi-use display device, determining that no ultrasound probe is available for connection; and
in response to the multi-use display device determining that no ultrasound probe is available for connection,
the multi-use display device accessing a demonstration ultrasound dataset;
the multi-use display device displaying the interactive demonstration of the ultrasound user interface with ultrasound data from the demonstration ultrasound dataset, the displaying being performed even though it is determined that no ultrasound probe is available for connection to the multi-use display device;
the multi-use display device receiving input on the interactive demonstration of the ultrasound user interface; and
the multi-use display device, in response to the received input, updating the interactive demonstration of the ultrasound user interface so that the ultrasound user interface corresponds to the received input, the updated ultrasound user interface appearing substantially similar to an appearance of the ultrasound user interface that is displayed if the received input is received during display of a live ultrasound image feed.

2. The method of claim 1, wherein when displaying the interactive demonstration of the ultrasound user interface, user interface controls for modifying image acquisition parameters are non-controllable.

3. The method of claim 1, wherein the demonstration ultrasound dataset is acquired at a single imaging depth.

4. The method of claim 3, wherein the received input comprises changing the imaging depth of the displayed ultrasound data from a first imaging depth to a second imaging depth, and updating the interactive demonstration of the ultrasound user interface comprises performing a digital zoom operation.

5. The method of claim 1, further comprising:
accessing another demonstration ultrasound dataset; and
when updating the interactive demonstration of the ultrasound user interface so that the ultrasound user interface corresponds to the received input, displaying additional ultrasound data from the another demonstration ultrasound dataset.

6. The method of claim 5, wherein the demonstration ultrasound dataset is acquired at a first imaging depth, and the another demonstration ultrasound dataset is acquired at a second imaging depth different from the first imaging depth, and the received input comprises changing the imaging depth from that of the demonstration ultrasound dataset to that of the another demonstration ultrasound dataset.

7. The method of claim 5, wherein prior to the accessing the another demonstration ultrasound dataset, the method further comprises:
determining if the received input requires downloading the another demonstration ultrasound dataset; and
if determined that the received input requires downloading the another demonstration ultrasound dataset, requesting and receiving the another demonstration ultrasound dataset from a server.

8. The method of claim 5, wherein the demonstration ultrasound dataset and the another demonstration ultrasound dataset are provided together in a demonstration ultrasound dataset collection prior to the receiving of the input on the interactive demonstration of the ultrasound user interface.

9. The method of claim 7, wherein the receiving of the another demonstration ultrasound dataset is performed as the ultrasound data from the demonstration ultrasound dataset is displayed.

10. The method of claim 1, wherein the demonstration ultrasound dataset is associated with a demonstration workflow.

11. The method of claim 10, wherein prior to accessing the demonstration ultrasound dataset, the method further comprises:
accessing a list of demonstration workflows;
displaying the list of demonstration workflows; and
receiving input selecting the demonstration workflow.

12. The method of claim 10, wherein the demonstration workflow is associated with a virtual demonstration imaging device, and prior to accessing the demonstration ultrasound dataset, the method further comprises:
accessing a list of virtual demonstration imaging devices;
displaying the list of virtual demonstration imaging devices; and
receiving input selecting the virtual demonstration imaging device associated with the virtual demonstration workflow.

13. A multi-use display device, that is configured to be used with an ultrasound probe that transmits and receives ultrasound energy for generating ultrasound images for display on the multi-use display device, comprising one or more processors and memory storing instructions for providing an interactive demonstration of an ultrasound user interface, wherein when the instructions are executed by the one or more processors, the one or more processors are configured to:
determine that no ultrasound probe is available for connection; and
in response to the determining that no ultrasound probe is available for connection, the one or more processors of the multi-use display device being further configured to:
access a demonstration ultrasound dataset;
display the interactive demonstration of the ultrasound user interface on the multi-use display device, the ultrasound user interface comprising ultrasound data from the demonstration ultrasound dataset, and the displaying being performed even though it is determined that no ultrasound probe is available for connection to the multi-use display device;
receive input on the interactive demonstration of the ultrasound user interface; and
in response to the received input, update the interactive demonstration of the ultrasound user interface so that the ultrasound user interface corresponds to the received input, the updated ultrasound user interface appearing substantially similar to an appearance of the ultrasound user interface that is displayed if the received input is received during display of a live ultrasound image feed.

14. The multi-use display device of claim 13, wherein the one or more processors are further configured to:
access another demonstration ultrasound dataset; and when updating the interactive demonstration of the ultrasound user interface so that the ultrasound user interface corresponds to the received input, display additional ultrasound data from the another demonstration ultrasound dataset.

15. The multi-use display device of claim 14, wherein the demonstration ultrasound dataset is acquired at a first imaging depth, and the another demonstration ultrasound dataset is acquired at a second imaging depth different from the first imaging depth, and the received input comprises changing the imaging depth from that of the demonstration ultrasound dataset to that of the another demonstration ultrasound dataset.

16. The multi-use display device of claim 14, wherein prior to the accessing the another demonstration ultrasound dataset, the one or more processors are further configured to:
   determine if the received input requires downloading the another demonstration ultrasound dataset; and
   if determined that the received input requires downloading the another demonstration ultrasound dataset, request and receive the another demonstration ultrasound dataset from a server.

17. The multi-use display device of claim 14, wherein the demonstration ultrasound dataset and the another demonstration ultrasound dataset are provided together in a demonstration ultrasound dataset collection, prior to the receiving of the input on the interactive demonstration of the ultrasound user interface.

18. The multi-use display device of claim 16, wherein the receiving of the another demonstration ultrasound dataset is performed as the ultrasound data from the demonstration ultrasound dataset is displayed.

19. The multi-use display device of claim 14, wherein the demonstration ultrasound dataset is associated with a demonstration workflow.

20. A non-transitory computer readable medium storing instructions for providing an interactive demonstration of an ultrasound user interface, wherein when the instructions are executed by one or more processors of a multi-use display device, that is configured to be used with an ultrasound probe that transmits and receives ultrasound energy for generating ultrasound images for display on the multi-use display device, the one or more processors are configured to:
   determine that no ultrasound probe is available for connection; and
   in response to the determining that no ultrasound probe is available for connection, the one or more processors being further configured to:
   access a demonstration ultrasound dataset;
   display the interactive demonstration of the ultrasound user interface on the multi-use display device, the ultrasound user interface comprising ultrasound data from the demonstration ultrasound dataset, and the displaying being performed even though it is determined that no ultrasound probe is available for connection to the multi-use display device;
   receive input on the interactive demonstration of the ultrasound user interface; and
   in response to the received input, update the interactive demonstration of the ultrasound user interface so that the ultrasound user interface corresponds to the received input, the updated ultrasound user interface appearing substantially similar to an appearance of the ultrasound user interface that is displayed if the received input is received during display of a live ultrasound image feed.

* * * * *